US00PP35344P2

(12) United States Plant Patent
Clark

(10) Patent No.: US PP35,344 P2
(45) Date of Patent: Aug. 22, 2023

(54) ***COLEUS* PLANT NAMED 'UF20-93-9'**

(50) Latin Name: *Coleus scutellarioides*
Varietal Denomination: UF20-93-9

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/803,899

(22) Filed: Jan. 13, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469, 373
CPC ... A01H 5/12; A01H 5/00; A01H 6/50; A01H 6/00
See application file for complete search history.

(56) References Cited

U.S. PATENT DOCUMENTS

PP27,269 P3 10/2016 Clark et al.
PP33,533 P2 * 9/2021 Clark ..... A01H 6/50 Plt./469

* cited by examiner

*Primary Examiner* — June Hwu
(74) *Attorney, Agent, or Firm* — Koenig IP Works, PLLC; Katherine Koenig

(57) ABSTRACT

A new and distinct cultivar of *Coleus* (*Coleus scutellarioides*) plant named 'UF20-93-9' selected for having a combination of desirable traits that make it well-suited for good performance as an annual plant in the summer landscape. 'UF20-93-9' has foliage that is consistent bright reddish orange, surrounded by well-defined chartreuse leaf margins. This bi-colored combination is novel, and 'UF20-93-9' maintains both colors in a wide range of garden light conditions. 'UF20-93-9' has exceptional vigor, and grows wider than tall, making it a plant that fills large gaps of summer garden space with consistent colors. It is extremely vigorous, highly branched and uniform in shape. These characters allow propagators to quickly produce many cuttings, and growers to produce large crops efficiently.

5 Drawing Sheets

Genus and species: *Coleus scutellarioides.*
Cultivar denomination:
'UF20-93-9'.

BACKGROUND OF THE NEW CULTIVAR

The invention relates to a new and distinct cultivar of *Coleus* plant named 'UF20-93-9'. The new cultivar 'UF20-93-9' originated from an open pollination conducted in May-November 2019 in Gainesville, Fla., between the female *Coleus* plant 'UF19-63-3' (unpatented) and an unknown male *Coleus* plant. A single seedling was chosen in May 2019 for further asexual propagation in Gainesville, Fla.

The new cultivar 'UF20-93-9' has been reproduced asexually for over 18 months through vegetative meristem tip cuttings and has been found to retain its distinctive characteristics through successive asexual propagations. 'UF20-93-9' was first propagated asexually by vegetative meristem tip cuttings in May 2019 in Gainesville, Fla., and has remained true-to-type since that time.

Plant Breeder's Rights for the new cultivar 'UF20-93-9' have not been applied for, and 'UF20-93-9' has not been made publicly available more than one year prior to the filing date of this application.

When compared to the female parent 'UF19-63-3', 'UF20-93-9' has larger leaves that are uniformly colored bright reddish orange with contrasting chartreuse (yellow green) accents at the leaf margins, whereas 'UF19-63-3' has smaller leaves colored burnt orange with lime green margins and accents. Furthermore, 'UF20-93-9' is more uniform and more vigorous, grows more wide than tall, and has a compact, upright and spreading habit with more lateral branching, whereas 'UF19-63-3' is less vigorous, and more upright in habit with less lateral branching.

The new cultivar 'UF20-93-9' was selected because it performs well in sun and shade and has excellent vigor to withstand the harsh selection conditions plants are subjected to in sun and shade trials in central Florida. 'UF20-93-9' is exceptional because it maintains bright reddish orange foliage color with consistent chartreuse margins in both sun and shade. It also has excellent overall plant vigor and well-branched uniformly compact, upright and spreading habit that is not common in *Coleus* plants having a significant amount of reddish orange colored foliage. 'UF20-93-9' has not been observed to flower in any trials to date, thus it provides long-lasting annual color in warm summer gardens and landscapes.

SUMMARY OF THE INVENTION

The new cultivar 'UF20-93-9' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF20-93-9' when grown under normal horticultural practices in Gainesville, Fla.: 'UF20-93-9' has the combination of vigorous, compact, upright and spreading growth habit, excellent heat tolerance, and bright reddish orange-colored leaves with chartreuse colored leaf margins, which is significantly different than other *Coleus* cultivars; 'UF20-93-9' has superior stability in foliage color in both sun and shade conditions; it has excellent lateral branching, making it suitable for propagators and producers; and 'UF20-93-9' has been observed to have long-season performance in landscape trials in Gainesville, Fla.

DESCRIPTION OF THE FIGURES

This new *Coleus* cultivar 'UF20-93-9' is illustrated by the accompanying photographs, which show the plant's form and foliage. The colors shown are as true as can be reasonaby obtained by conventional photographic procedures.

FIG. 2 shows the growth habit, form, and foliage of the new *Coleus* cultivar;

FIG. 3 shows a close-up view of the foliage of the new *Coleus* cultivar;

FIG. 4 shows the adaxial side of an immature leaf (left) and a mature leaf (right) of the new *Coleus* cultivar with corresponding RHS color designations; and FIG. 5 shows the abaxial side of an immature leaf (left) and a mature leaf (right) of the new *Coleus* cultivar with corresponding RHS color designations.

DETAILED BOTANICAL DESCRIPTION OF THE CULTIVAR

Figure 1:
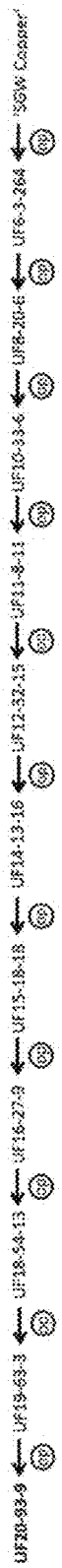
FIG. 1 shows the pedigree of the new *Coleus* cultivar 'UF20-93-9' shown and described herein.
Figure 2:
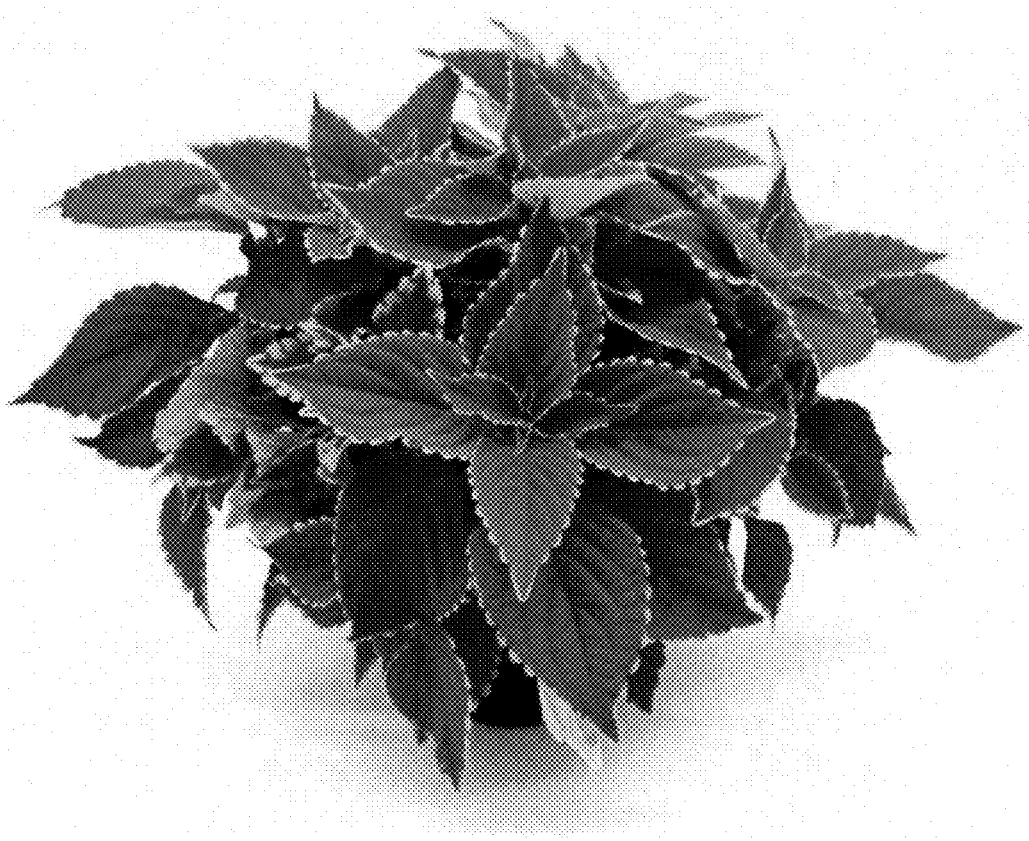
FIGS. 2-5 were taken from plants grown ten weeks from unrooted cuttings in February-April 2022 in a glass-covered greenhouse in Gainesville, Fla.
Figure 3:
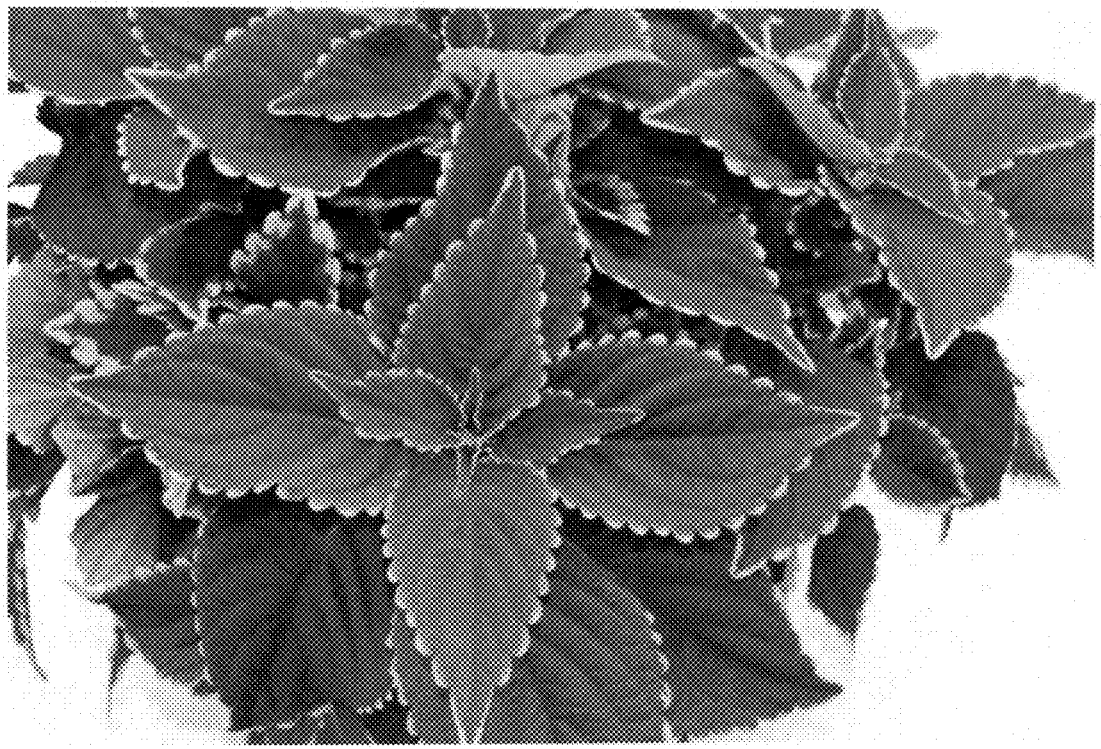
Figure 4:
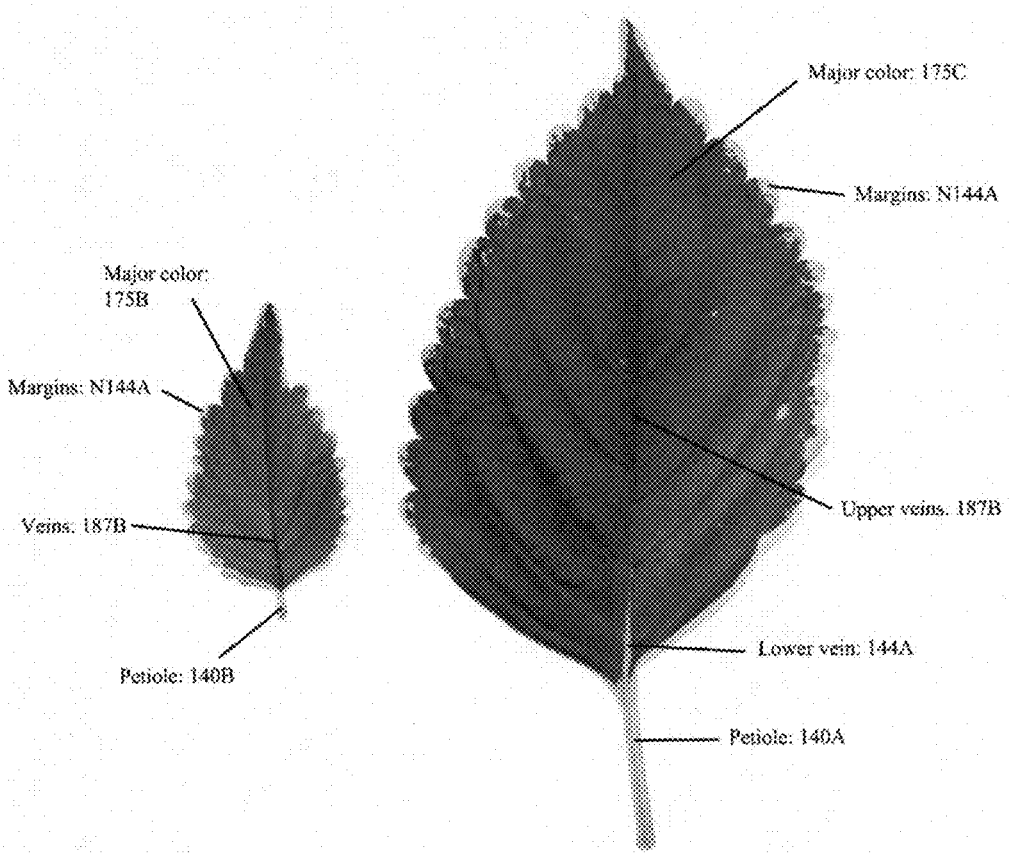
Figure 5:
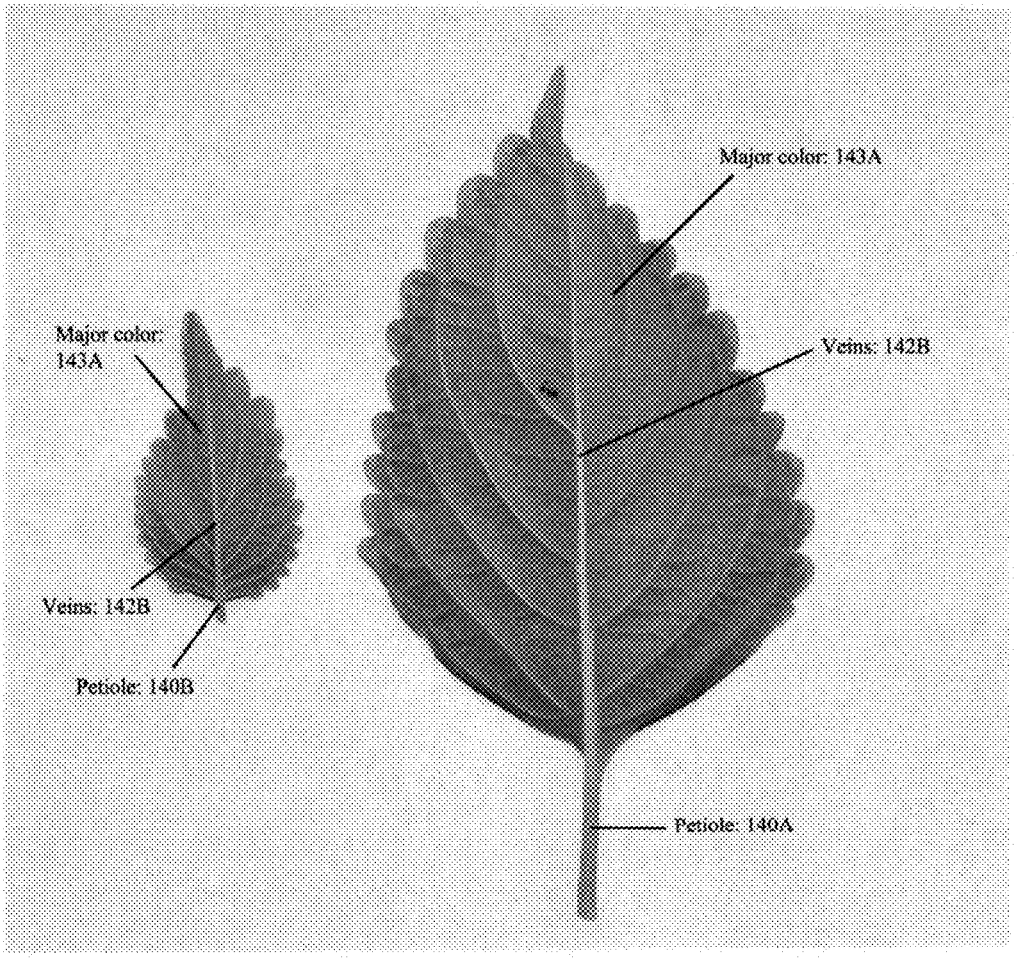

Foliage color was determined under full sun conditions in the middle of the day in a glass-covered greenhouse. Color references are to The RHS Colour Chart of The Royal Horticultural Society of London (RHS), 2007 5th Edition. *Coleus* leaves are rarely one solid color but encompass hues, shades and tints, and color patterns differ from one genotype to another due to varying levels of variegation. The following detailed description of 'UF20-93-9' was obtained using ten-week-old plants grown from unrooted cuttings in February-April 2022 in a glass-covered greenhouse in Gainesville, Fla. The plants were propagated in mist for ten days after cuttings were stuck, then grown in one-gallon pots for approximately eight and a half additional weeks.

Botanical Description

Botanical classification:

*Family.*—Lamiaceae.

*Botanical name.*—*Coleus scutellarioides.*

*Common name.*—*Coleus.*

*Cultivar.*—'UF20-93-9'.

Parentage:

*Female or seed parent.*—'UF19-63-3'.

*Male or pollen parent.*—Unknown.

Propagation:

*Type cuttings.*—Vegetative meristem tip cuttings having at least 1 node.

*Time to initiate roots.*—3-4 days.

*Time to produce a rooted cutting.*—7-10 days.

*Root habit.*—Fibrous.

*Root description.*—Callus forms in 2-3 days, roots initiate in 3-4 days and become a highly branched cutting in 7-10 days.

Plant description:

*Habit.*—Compact, upright, and spreading.

*Height* (*from top of soil*).—28-32 cm.

*Width* (*horizontal plant diameter*).—70-75 cm.

Branches:

*Quantity per plant.*—Approximately 13.

*Branch color.*—RHS 143B (yellow green).

*Texture.*—Smooth.

*Pubescence.*—Not present.

*Stem description.*—Square-shaped stem.

*Branch diameter.*—0.9-1.0 cm at the base of a 25-cm-long branch.

*Branch length.*—25-28 cm.

*Internode length.*—3 cm measured at mid-branch.

*Anthocyanin.*—Not present.

Leaves:

*Quantity of leaves per branch.*—18-20.

*Arrangement.*—Opposite.

*Fragrance.*—Not fragrant.

*Shape.*—Ovate.

*Length.*—15-16 cm.

*Width.*—10-11 cm.

*Apex.*—Broadly acute.

*Base.*—Attenuate.

*Margin.*—Crenate.

*Leaf texture.*—Upper surface: Pulverulent. Lower surface: Smooth.

*Venation color, mature leaf.*—Upper surface, major color: RHS 187B (dark red). Upper surface, base: RHS 144A (yellow green). Lower surface: RHS 142B (yellow green).

*Venation color, immature leaf.*—Upper surface: RHS 187B (dark red). Lower surface: RHS 142B (yellow green).

*Venation pattern.*—Upper surface: Reticulate. Lower surface: Reticulate.

*Color: Immature leaf.*—Upper surface, major color: RHS 175B (reddish orange). Upper surface, margins: RHS N144A (yellow green). Lower surface, major color: RHS 143A (yellow green).

*Color: Mature leaf.*—Upper surface, major color: RHS 175C (reddish orange). Upper surface, margins: RHS N144A (yellow green). Lower surface, major color: RHS 143A (yellow green).

*Petiole length.*—4-5 cm.

*Petiole diameter.*—0.3-0.4 cm.

*Petiole color, mature leaf.*—RHS 140A (yellowish green).

*Petiole color, immature leaf.*—RHS 140B (yellowish green).

*Petiole texture.*—Smooth, no pubescence.

Flowers and seeds: Flowers and seeds have not been observed to date during formal trials in Gainesville, Fla.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla., have been long-tailed or citrus mealybugs (*Pseudococcus* spp.), which occur on older stock plant material held in the greenhouse for over 3-4 months. Impatiens Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

Comparison with Known Cultivars

When the new cultivar 'UF20-93-9' is compared to the commercial cultivar 'UF12-22-1' (U.S. Plant Pat. No. 27,269, commercial name "Campfire"), 'UF20-93-9' has leaves colored reddish orange with a thin yellow green coloration along the leaf margins, whereas 'UF12-22-1' has leaves colored entirely reddish brown with no yellow green coloration along the leaf margins.

What is claimed is:

1. A new and distinct *Coleus scutellarioides* plant named 'UF20-93-9' as shown and described herein.

* * * * *